(12) United States Patent
Wollenweber

(10) Patent No.: US 8,761,467 B2
(45) Date of Patent: Jun. 24, 2014

(54) METHOD AND APPARATUS FOR ASSESSING MOTION CORRECTION

(75) Inventor: Scott David Wollenweber, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 559 days.

(21) Appl. No.: 12/897,512

(22) Filed: Oct. 4, 2010

(65) Prior Publication Data

US 2012/0082350 A1 Apr. 5, 2012

(51) Int. Cl.
*G06K 9/00* (2006.01)

(52) U.S. Cl.
USPC .......................................................... 382/128

(58) Field of Classification Search
None
See application file for complete search history.

(56) References Cited

U.S. PATENT DOCUMENTS

| | | | |
|---|---|---|---|
| 5,961,610 A | 10/1999 | Kelly et al. | |
| 7,503,009 B2 * | 3/2009 | Peters | 715/764 |
| 7,936,910 B2 * | 5/2011 | Watt | 382/128 |
| 2002/0054172 A1 * | 5/2002 | Berman et al. | 345/856 |
| 2006/0178575 A1 * | 8/2006 | Piacsek et al. | 600/413 |
| 2006/0291621 A1 * | 12/2006 | Yan et al. | 378/65 |
| 2007/0177780 A1 * | 8/2007 | Chui | 382/128 |
| 2007/0214017 A1 | 9/2007 | Profio et al. | |
| 2008/0170654 A1 * | 7/2008 | Tkaczyk et al. | 378/8 |
| 2008/0180098 A1 * | 7/2008 | Takei | 324/309 |
| 2008/0228522 A1 | 9/2008 | Davis et al. | |
| 2009/0163799 A1 * | 6/2009 | Erbel et al. | 600/424 |
| 2009/0182576 A1 | 7/2009 | Warner et al. | |
| 2009/0249210 A1 * | 10/2009 | Sheldon et al. | 715/730 |
| 2009/0285466 A1 * | 11/2009 | Hipp et al. | 382/131 |
| 2010/0131482 A1 | 5/2010 | Linthicum et al. | |
| 2010/0131498 A1 | 5/2010 | Linthicum et al. | |
| 2010/0131883 A1 | 5/2010 | Linthicum et al. | |
| 2010/0166274 A1 * | 7/2010 | Busch et al. | 382/131 |
| 2011/0161112 A1 * | 6/2011 | Keefe et al. | 705/3 |
| 2011/0206178 A1 * | 8/2011 | Van Herk et al. | 378/19 |

OTHER PUBLICATIONS

S. S. Vedam, P J Keall2,V R Kini2, HMostafavi3, H P Shukla4 and R Mohan, "Acquiring a four-dimensional computed tomography dataset using an external respiratory signal" Phys. In Medicine and Biology, 4B. 2003.*

Guoping Chang, Tingting Chang, and John W. Clark, Jr., Osama R. Mawlawia. "Implementation of an Automated respiratory amplitude gating device for PET/CT: Clinical Evaluation" The Journal of Nuclear Medicine, vol. 51. Jan. 2010, hereinafter Chang.*

* cited by examiner

*Primary Examiner* — Barry Drennan
*Assistant Examiner* — Oneal R Mistry
(74) *Attorney, Agent, or Firm* — The Small Patent Law Group; Dean D. Small

(57) ABSTRACT

A method for evaluating the effectiveness of a motion correction procedure includes acquiring an imaging dataset of an object using an imaging system, identifying a motion affected portion of the imaging dataset, motion correcting the identified portion to generate a motion corrected imaging dataset, and displaying both the identified portion and the motion corrected imaging dataset on a display device in a comparable manner or format. A system and computer readable medium for implementing the method are also described herein.

23 Claims, 5 Drawing Sheets

METHOD AND APPARATUS FOR ASSESSING MOTION CORRECTION

BACKGROUND OF THE INVENTION

The subject matter disclosed herein relates generally to imaging systems, and more particularly to an apparatus and method for displaying medical images.

Multi-modality imaging systems exist that scan using different modalities, for example. Computed Tomography (CT), Magnetic Resonance Imaging (MRI), Positron Emission Tomography (PET), and Single Photon Emission Computed Tomography (SPECT). During operation, the image quality of the conventional imaging systems may be affected by the motion of the object being imaged. In particular, motion of the imaged object can degrade the image quality. More specifically, image artifacts are produced by movement of the object during image acquisition. Respiratory motion is a common source of involuntary motion in mammals (e.g., people and animals) encountered in medical imaging systems. The respiratory motion may lead to errors during image review, such as when a physician is determining the size of a lesion, determining the location of the lesion, or quantifying the lesion.

At least one conventional imaging system utilizes various techniques to correct for motion related imaging artifacts. However, the quantity of motion-corrected data produced by utilizing the various techniques is typically relatively large. As a result, it is often time consuming for the operator to identify which images have been motion-corrected. Moreover, it is often difficult to determine the effectiveness of the motion correction procedure.

BRIEF DESCRIPTION OF THE INVENTION

In one embodiment, a method for evaluating the effectiveness of a motion correction procedure is provided. The method includes acquiring an imaging dataset of an object using an imaging system, identifying a motion affected portion of the imaging dataset, motion correcting the identified portion to generate a motion corrected imaging dataset, and displaying both the identified portion and the motion corrected imaging dataset on a display device in a comparable manner or format. A system and computer readable medium for implementing the method are also described herein.

In another embodiment, a medical imaging system is provided. The medical imaging system includes a first modality unit and a computer operationally coupled to the first modality unit. The computer is programmed to acquire an imaging dataset of an object using the medical imaging system, identify a motion affected portion of the imaging dataset, motion correct the identified portion to generate a motion corrected imaging dataset, and display both the identified portion and the motion corrected imaging dataset on a display device in a comparable manner or format.

In a further embodiment, a non-transitory computer readable medium encoded with a program is provided. The program is programmed to instruct a computer to acquire an imaging dataset of an object using the medical imaging system, identify motion affected portion of the imaging dataset, motion correct the identified portion to generate a motion corrected imaging dataset, and display both the identified portion and the motion corrected imaging dataset on a display device in a comparable manner or format.

DETAILED DESCRIPTION OF THE INVENTION

Figure 1:
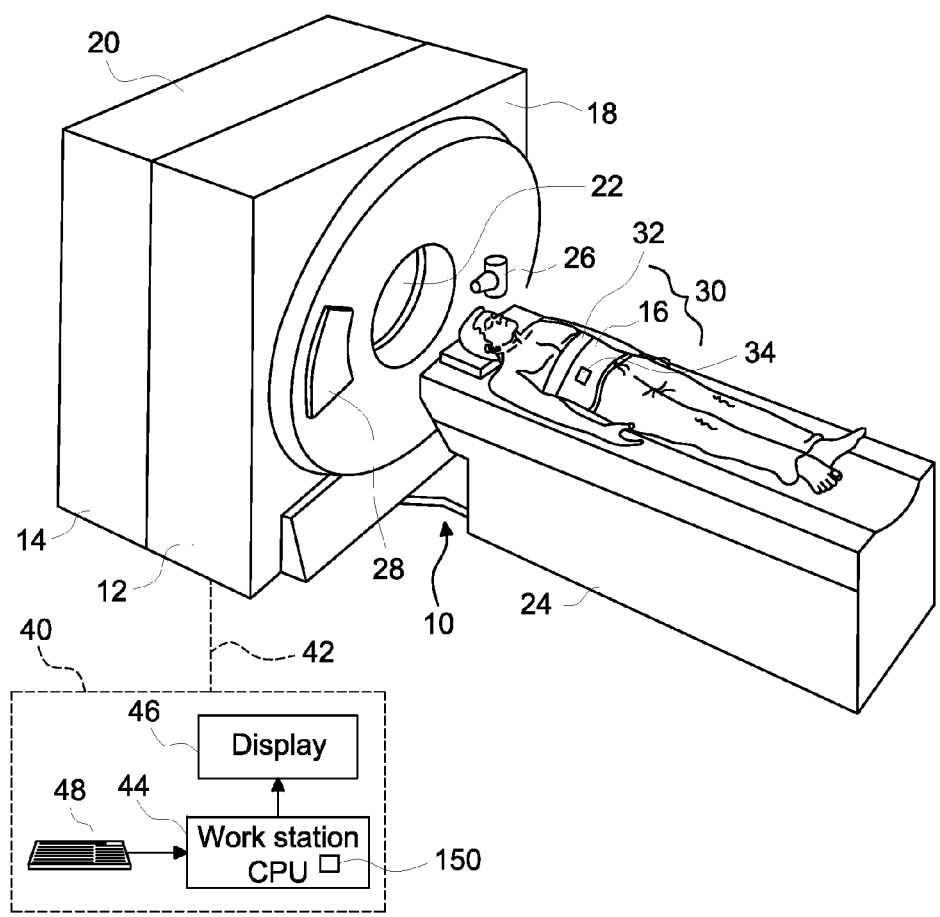
FIG. 1 is a pictorial view of an exemplary multi-modality imaging system formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

Various embodiments described herein provide a multi-modality imaging system 10 as shown in FIG. 1. The multi-modality imaging system 10 may be any type imaging system, for example, different types of medical imaging systems, such as a Positron Emission Tomography (PET), a Single Photon Emission Computed Tomography (SPECT), a Computed Tomography (CT), an ultrasound system, Magnetic Resonance Imaging (MRI) or any other system capable of generating diagnostic images. The various embodiments are not limited to multi-modality medical imaging systems, but may be used on a single modality medical imaging system such as a stand-alone PET imaging system, a stand-alone CT imaging system, an Magnetic Resonance Imaging (MRI), and a Photon Emission Computed Tomography (SPECT), for example. Moreover, the various embodiments are not limited to medical imaging systems for imaging human subjects, but may include veterinary or non-medical systems for imaging non-human objects, etc.

Referring to FIG. 1, the multi-modality imaging system 10 includes a first modality unit 12 and a second modality unit 14. The two modality units enable the multi-modality imaging system 10 to scan an object or patient 16 in a first modality using the first modality unit 12 and to scan the patient 16 in a second modality using the second modality unit 14. The multi-modality imaging system 10 allows for multiple scans in different modalities to facilitate an increased diagnostic capability over single modality systems. In one embodiment, the multi-modality imaging system 10 is a CT/PET imaging system 10, e.g. the first modality 12 is a CT imaging system and the second modality 14 is a PET imaging system. The imaging system 10 is shown as including a gantry 18 that is associated with the CT imaging system 12 and a gantry 20 that is associated with the PET imaging system 14. During operation, the patient 16 is positioned within a central opening 22, defined through the imaging system 10, using, for example, a motorized table 24.

The gantry 18 includes an x-ray source 26 that projects a beam of x-rays toward a detector array 28 on the opposite side of the gantry 18. The detector array 28 is formed by a plurality of detector rows (not shown) including a, plurality of detector elements which together sense the projected x-rays that pass through the patient 16. Each detector element produces an electrical signal that represents the intensity of an impinging x-ray beam and hence allows estimation of the attenuation of the beam as the beam passes through the patient 16. During a scan to acquire x-ray attenuation data, the gantry 18 and the components mounted thereon rotate about a center of rotation. Additionally, the PET imaging system includes a detector (not shown) that is configured to acquire emission data.

The imaging system 10 also includes at least one motion sensor 30 that is adapted to detect and transmit information that is indicative of the motion of the patient 16. In one embodiment, the motion sensor 30 may be embodied as a belt-type motion sensor 32 that is adapted to extend at least partially around the patient 16. Optionally, the motion sensor 30 may be embodied as a motion sensor 34 that is adapted to be secured to a predetermined position on the patient 16. It should be realized that although two different motion sensors are described, that the imaging system 10 may include other types of motions sensors to generate motion related information of the patient 16.

The imaging system 10 also includes an operator workstation 40. During operation, the motorized table 24 moves the patient 16 into the central opening 22 of the gantry 18 and/or 20 in response to one or more commands received from the operator workstation 40. The workstation 40 then operates the first and second modalities 12 and 14 to both scan the patient 16 and acquire attenuation and/or emission data of the patient 16. The workstation 40 may be embodied as a personal computer (PC) that is positioned near the imaging system 10 and hard-wired to the imaging system 10 via a communication link 42. The workstation 40 may also be embodied as a portable computer such as a laptop computer or a hand-held computer that transmits information to, and receives information from, the imaging system 10. Optionally, the communication link 42 may be a wireless communication link that enables information to be transmitted to or from the workstation 40 to the imaging system 10 wirelessly. In operation, the workstation 40 is configured to control the operation of the imaging system 10 in real-time. The workstation 40 is also programmed to perform medical image diagnostic acquisition and reconstruction processes described herein.

The operator workstation 40 includes a central processing unit (CPU) or computer 44, a display 46, and an input device 48. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 44 executes a set of instructions that are stored in one or more storage elements or memories, in order to process information received from the first and second modalities 12 and 14. The storage elements may also store data or other information as desired or needed. The storage element may be in the form of an information source or a physical memory element located within the computer 44.

The set of instructions may include various commands that instruct the computer 44 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The computer 44 connects to the communication link 42 and receives inputs, e.g., user commands, from the input device 48. The input device 48 may be, for example, a keyboard, mouse, a touch-screen panel, and/or a voice recognition system, etc. Through the input device 48 and associated control panel switches, the operator can control the operation of the CT imaging system 12 and the PET imaging system 14 and the positioning of the patient 16 for a scan. Similarly, the operator can control the display of the resulting image on the display 46 and can perform image-enhancement functions using programs executed by the computer 44.

Figure 2:
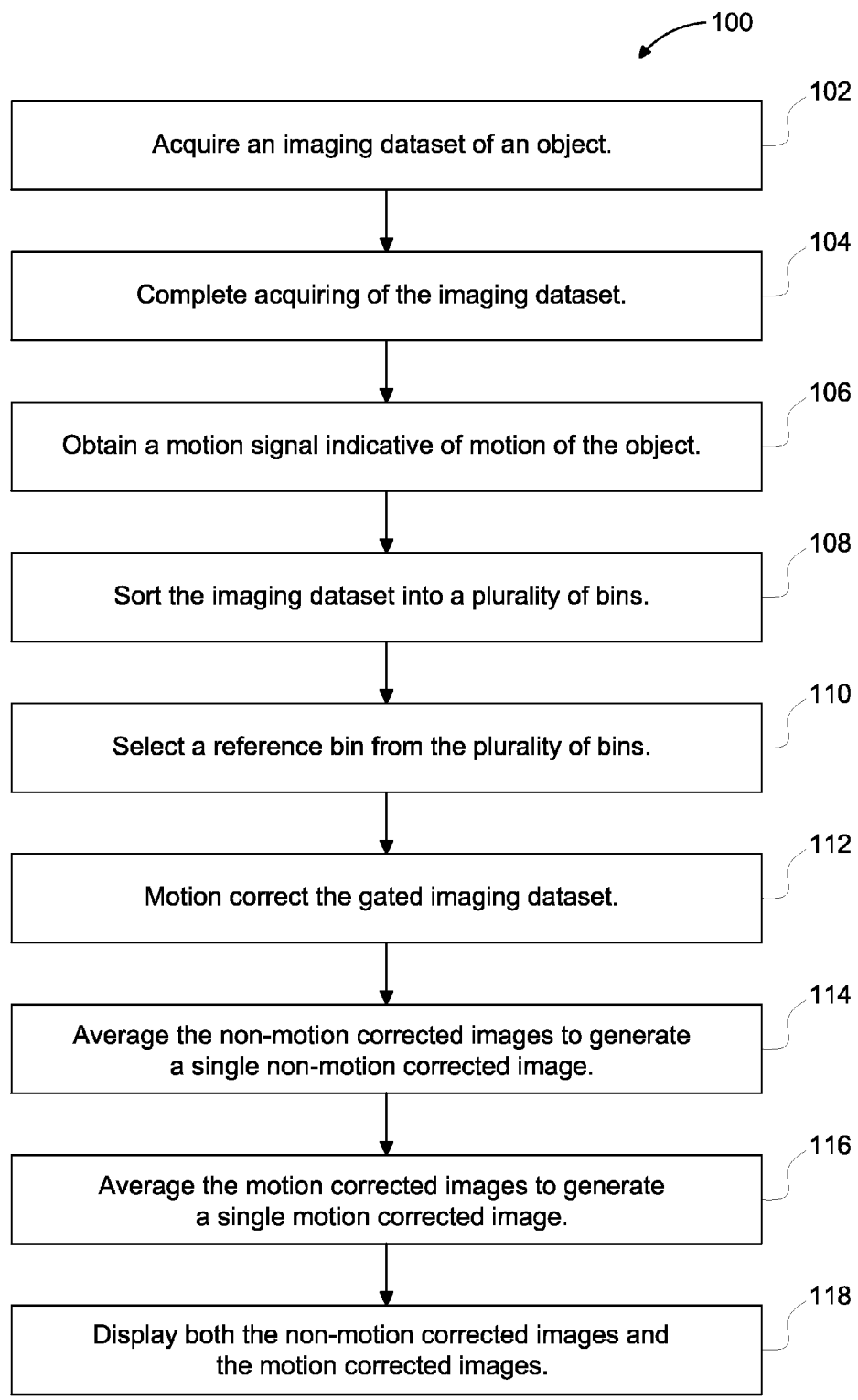
FIG. 2 is a flowchart illustrating a method for evaluating the effectiveness of a motion correction procedure in accordance with various embodiments.

FIG. 2 is a simplified block diagram of an exemplary method 100 for determining the effectiveness of a motion correction procedure. Specifically, the method 100 enables the operator to design custom dashboards that display sets of images. The term 'dashboard' is used to describe the display of information from mixed sources, such as images, text, graphs, or charts, aimed at enabling an operator to view in one place the relevant information to make a decision. The sets of images may be selected by the operator and arranged on the display in a format that enables the operator to visually compare the different sets of images with each other. The images may be positioned or formatted from top to bottom on the display, from side to side on the display, or any other visual arrangement. Based on the comparison, the operator may determine the effectiveness of a motion correction procedure. It should be realized that in the exemplary embodiment, the comparison is performed visually by an operator. Optionally, the comparison may be performed automatically by a computer. In the exemplary embodiment, the method 100 is performed by the imaging system 10 shown in FIG. 1 and may be implemented by the computer 44 in accordance with various embodiments. The method 100 is utilized to display both motion corrected information and non-motion corrected information. Thus, in various embodiments, the method 100 reduces the quantity of information that a physician is required to review to determine the effectiveness of the motion correction procedure.

Referring again to FIG. 2, at 102 an imaging dataset of an object, such as the patient 16, is acquired using an imaging system, such as, for example the imaging system 10. In the exemplary embodiment, acquiring the imaging dataset includes scanning the patient 16 to acquire a transmission dataset and/or an emission dataset of the patient 16, or a region of the patient 16. In one embodiment, the CT imaging system 12 may be utilized to perform a scout scan of the patient 16. The scout scan may be performed over a relatively short duration to produce a single 2D image (not shown) that is similar to an x-ray of the patient 16. The internal motion information of the patient 16 may be determined by viewing the imaging dataset 150 (shown in FIG. 1).

The information acquired from the scout scan may then be utilized to select a scan range that includes a volume of interest to be motion corrected. In one embodiment, an exemplary volume of interest (not shown) is selected manually by the operator after reviewing the scout scan image. Optionally, the volume of interest may be selected automatically by the imaging system 10 by comparing the scan data utilized to generate the scout image to historical scan data. In another option, the volume of interest may be manually selected by the operator based on a priori operator information. For example, the operator may have knowledge where motion typically occurs during the imaging procedure or is more likely to occur. Based in this information, the operator may then manually select the volume of interest to be motion corrected. After the scan range has been selected, the object is scanned at 102. Optionally, acquiring at 102 may include using information that has been stored in a computer of a previously performed scan.

At 104, the acquiring of the image dataset is completed. As a result of the scanning procedure described at 102, the imaging dataset 150 (shown in FIG. 1) of the patient 16 is generated. In one embodiment, the imaging dataset 150 represents information generated during a scanning procedure using the CT imaging system 12. In another embodiment, the imaging dataset 150 represents information generated during a scanning procedure using the PET imaging system 14.

Figure 3:
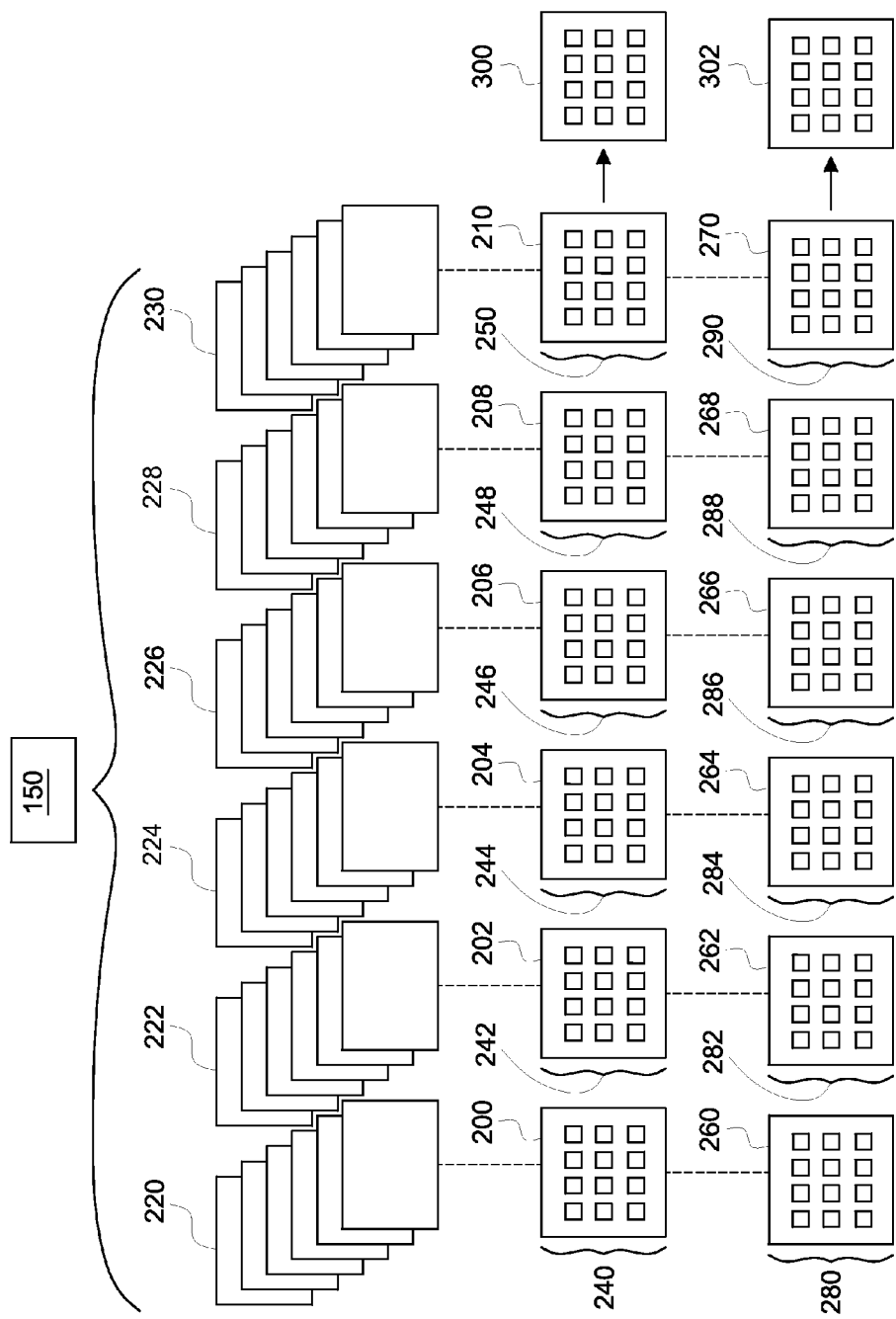
FIG. 3 is a simplified block diagram illustrating the method of FIG. 2 in accordance with various embodiments.

At 106, a signal indicative of motion (not shown) of the patient 16 is obtained. The motion signal may be obtained during the CT imaging scan at 102, during a related PET imaging scan, or during any other medical imaging system scanning procedure. Optionally, the motion signal may be obtained from a database of previous medical examination procedures or it may be derived from other data acquired during the scan, such as the raw data. In the exemplary embodiment, the motion signal is obtained using the motion sensor 30 shown in FIG. 1. Optionally, the motion signal may be obtained from information saved in a memory device located in the computer 44. In the exemplary embodiment, the motion signal is representative of the motion of the patient 16 within a selected volume of interest Referring again to FIG. 2, the method of performing the motion correction on the imaging dataset 150 is now discussed. At 108, the imaging dataset 150 is sorted or gated into n bins. For example, FIG. 3 is a simplified block diagram illustrating a plurality of bins numbered 200 . . . 210, i.e. n=6 bins. Thus, in the exemplary embodiment, the imaging dataset 150 sorted into the six bins numbered 200, 202, 204, 206, 208, and 210. However, it should be realized that the quantity of bins illustrated in FIG. 3 is exemplary, and that during operation, fewer than six bins or more than six bins may be utilized. As such, each bin 200, 202, 204, 206, 208, and 210 includes approximately ⅙ of the total information in the imaging dataset 150.

For example, assuming that the total length of the scan performed at 102 to acquire emission data is three minutes, moreover, assuming that the imaging dataset 150 is sorted into six bins, then each respective bin includes approximately 30 seconds of information. Thus a first portion 220 of the imaging dataset 150 is sorted into the bin 200, a second portion 222 of the imaging dataset 150 is sorted into the bin 202, a third portion 224 of the imaging dataset 150 is sorted into the bin 204, a fourth portion 226 of the imaging dataset 150 is sorted into the bin 206, a fifth portion 228 of the imaging dataset 150 is sorted into the bin 208, and a sixth portion 230 of the imaging dataset 150 is sorted into the bin 210.

In the exemplary embodiment, the imaging dataset 150 is sorted into a respective bin based on the motion state of the patient 16. Information to determine the motion state of the patient 16 may be acquired from, for example, the motion sensor 30. For example, the bin 200 may include imaging data acquired at the beginning of a respiration phase, and the bin 210 may include imaging data acquired at the end of the respiration phase. Moreover, each intervening bin, e.g. bins 202, 204, 206, and 208 may include imaging data that represents a motion state between inspiration and expiration. More specifically, each of the bins 200, 202, 204, 206, 208, and 210 are adapted to receive imaging data that was acquired over a plurality of breathing cycles. Moreover, each of the bins 200, 202, 204, 206, 208, and 210 are adapted to receive imaging data that represents approximately the same point in the patient's breathing cycle. Accordingly, each of the bins 200, 202, 204, 206, 208, and 210 include imaging data representing a certain motion state of the patient 16. In the exemplary embodiment, the motion information acquired from the motion sensor 30 is utilized to divide the imaging data 150 into six substantially equal portions and store the substantially equal portions in a respective bin 200, 202, 204, 206, 208, and 210. Thus, at the conclusion of the gating process at 108 a plurality of bins are formed and each respective bin 200 . . . 210 includes a plurality of two-dimensional (2D) images shown as images 240, 242, 244, 246, 248, and 250, respectively that are not motion corrected.

In another exemplary embodiment, the information that represents the imaging dataset 150 may be binned or sorted based on using a Quiescent Period Gating (QPG) algorithm. Quiescent as used herein refers to a respiratory state of relative inactivity, repose, and/or tranquility. The QPG algorithm may be implemented using, for example, computer 44. The QPG algorithm performs quiescent period gating on the imaging dataset 150 to account for the motion of a region of interest of the patient 16 based on a motion signal received from the motion sensor 30 shown in FIG. 1. More specifically, the QPG algorithm identifies the motion of the patient 16 and re-organizes the imaging dataset 150 to enable a motion-reduced image of the patient 16 to be reconstructed.

In operation, the QPG algorithm determines at least one quiescent period of at least a portion of the motion signal received from the motion sensor 30. The QPG algorithm utilizes the determined quiescent period to perform quiescent gating. For example, in one embodiment, the QPG algorithm utilizes the determined quiescent period to perform a displacement histogram-based gating of the imaging dataset 150. Specifically, the QPG algorithm divides the motion signal into intervals based on the displacement of the motion signal. The imaging dataset 150 is then sorted into one quiescent bin based on the displacement of the motion signal, forming a single set of 2D images as in 240. Optionally, the QPG algorithm utilizes the determined quiescent period to perform a cycle-based gating of the imaging dataset 150. During operation, the QPG algorithm is configured to extract image data from the imaging dataset 150 that corresponds to periods where, for each cycle, the motion signal is below or less than a predetermined threshold.

For example, a motion signal having significant amplitude variations and baseline shift may result in images that are not properly correlated or registered. The histogram-base method described above enables images with less motion signal variation to be generated. Moreover, when the motion signal does not have significant amplitude variation and baseline shift, the cycle based method may be utilized.

Referring again to FIG. 2, at 110, a reference bin is selected to further perform the motion correction on the imaging dataset 150 to generate motion corrected information. The reference bin may be selected manually by the operator. Optionally, the reference bin may be selected automatically by the computer 44. For example, the reference bin may be determined to be the bin 200.

At 112, the gated imaging dataset formed at 108 are corrected to substantially reduce or eliminate the effects of motion on the imaging dataset 150. In the exemplary embodiment, the motion correction is performed by registering the bins shown in FIG. 3 to a reference bin 200. More specifically, in the exemplary embodiment, the bins 202, 204, 206, 208 are and 210 are registered to the reference bin 200 which was selected at 110. The bins 202, 204, 206, 208, and 210 may be registered to the reference bin 200 using either a rigid or non-rigid registration. The rigid and non-rigid registrations may be performed manually by the operator or automatically by the computer 44.

In the exemplary embodiment, performing a non-rigid registration includes transforming the information within the bins 202, 204, 206, 208 and 210 in three-dimensional (3D) space to align the information within the bins 202, 204, 206, 208 and 210 to the reference bin 200. For example, the images in the bin 202 may be slighted tilted with respect to the images in the reference bin 200. Accordingly, the images within the bin 202 are tilted to align the images with the images in the reference bin 200. The remaining bins 204, 206, 208 and 210 are also realigned to substantially match the images in the reference bin 200. In operation, the rigid registration process may be implemented by selecting anatomical or other features/points/landmarks and the images aligned using these feature or points along with detected edges or borders within the images. Alternatively, different markers may be used to identify known anatomical locations. The rigid registration also may be based on curved contours, for example, of bones within the image. The rigid registration may also be volume based or surface based. However, it should be appreciated that any rigid registration process may be performed that includes optimizing or calculating a certain comparable criteria or similarity measure.

In another embodiment, a non-rigid registration procedure may be utilized to perform the motion correction on the imaging dataset 150. In operation, the non-rigid registration or elastic registration includes non-rigid transformations. These non-rigid transformations allow local warping of image features and provide registrations that account for local deformations.

Non-rigid transformation approaches include, for example, polynomial warping, interpolation of smooth basis functions (thin-plate splines and wavelets), and physical continuum models (viscous fluid models and large deformation diffeomorphisms). The non-rigid registration is performed using the images forming the imaging dataset 150. The non-rigid registration may include, for example, warping of points or landmarks and providing a best fit along a contour with interpolation and correlation of the points or landmarks. Alternatively, a blending process may be performed that compares image voxels and blends corresponding regions. In general, the local non-rigid registration includes any type of elastic deformation model that allows for variations or movements in the different image sets.

As a result of the motion correction procedure performed at 112, a plurality of bins that include motion corrected information are formed. In the exemplary embodiment, the gated information stored in bin 200 is stored in a bin 260 after the motion correction procedure is performed. Moreover, the gated information in bin 202 is stored in a bin 262, the gated information in bin 204 is stored in a bin 264, the gated information in bin 206 is stored in a bin 266, the gated information in bin 208 is stored in a bin 268, and the gated information in bin 210 is stored in a bin 270. As a result of the motion correction process, each respective bin 260 . . . 270 includes a plurality of 2D images 280, 282, 284, 286, 288, and 290 that are formed as a result of motion correcting the respective 2D images 240, 242, 244, 246, 248, and 250 stored in the bins 200 . . . 210, respectively.

Referring again to FIG. 2, at 114, the 2D images stored in the bins 200 . . . 210, i.e., the non-motion corrected images, are averaged together to generate a single non-motion corrected image 300 (shown in FIG. 3). More specifically, a single image from each of the bins 200 . . . 210 are averaged together to form a single image that is stored in the bin 300. Because, each bin in the exemplary embodiment includes twelve images, the bin 300 includes twelve images, wherein each image represents a different slice that is not motion corrected.

At 116, the 2D images stored in the bins 240 . . . 250, i.e., the motion corrected images, are averaged together to generate a single motion corrected image that is stored in 302 (shown in FIG. 3). More specifically, a single image from each of the bins 240 . . . 250 are averaged together to form a single image that is stored in the bin 300. Because, each bin in the exemplary embodiment includes twelve images, the bin 302 includes twelve images or slices.

At 118, both the identified portion of the imaging dataset 150 that is affected by motion 240 . . . 250 and the motion corrected imaging dataset 280 . . . 290 are displayed on a display device to enable an operator to determine the effectiveness of the motion correction procedure. As discussed above, it is often difficult for an operator to assess the effectiveness of a motion correction procedure because of the inability of the operator to efficiently and/or effectively evaluate the imaging data. Accordingly, various embodiments described herein facilitate enabling an operator to display a variety of imaging data simultaneously or concurrently on a single display, also referred to herein as a dashboard. Displaying the variety of information in a side-by-side or top-to-bottom arrangement enables the operator to observe both the non-motion corrected imaging data and the motion corrected imaging data concurrently to evaluate whether the motion correction algorithm was effective or not effective.

Figure 4:
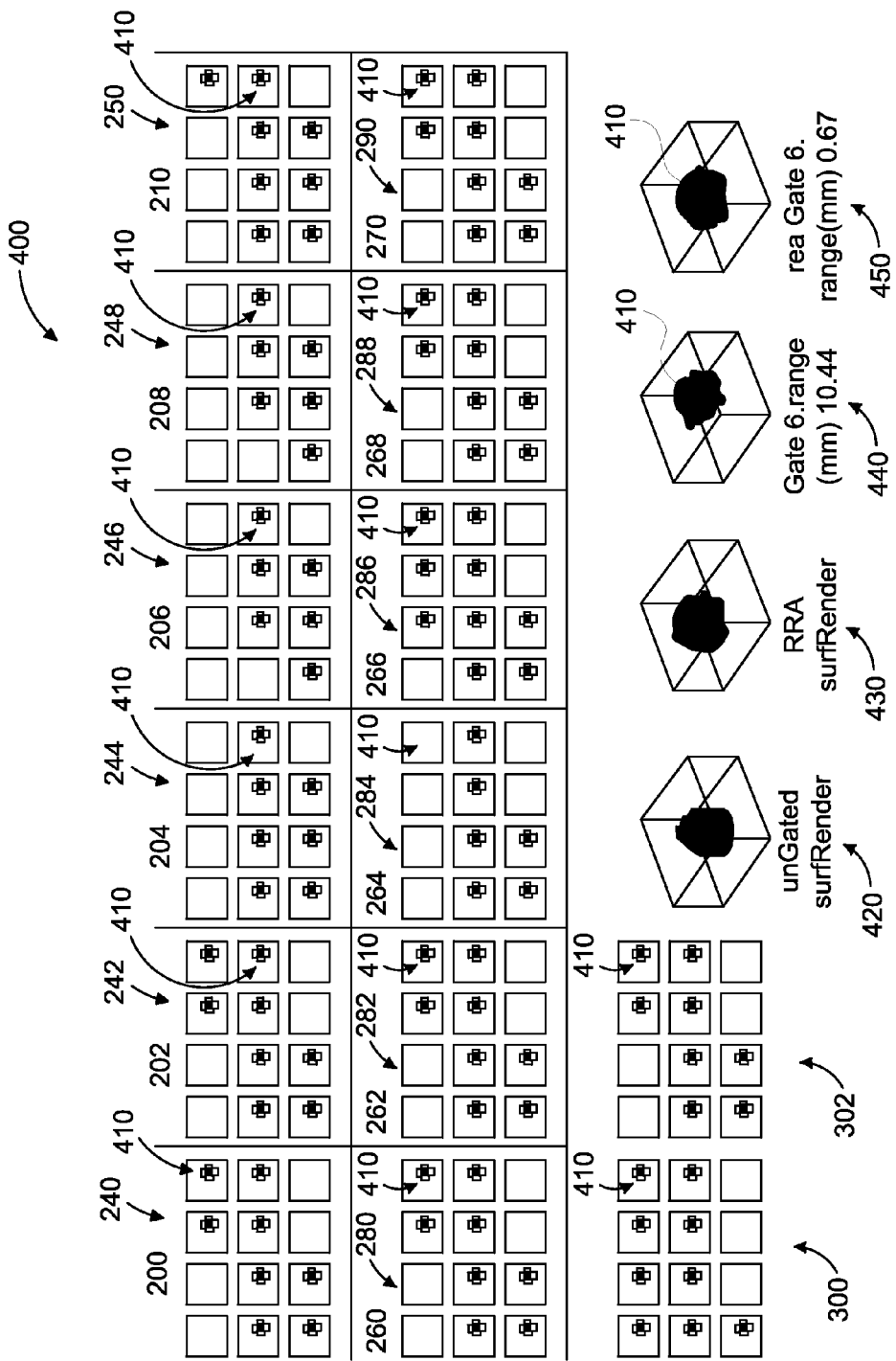
FIG. 4 is a dashboard that may be generated in accordance with various embodiments.

FIG. 4 is an exemplary dashboard 400 that may be generated at 118. The dashboard 400 is configured to display the non-motion corrected information stored in the bins 200 . . .

210. For example, as shown in FIG. 4, the bin 200 includes twelve 2D images 240, the bin 202 includes twelve 2D images 242, the bin 204 includes twelve 2D images 244, the bin 206 includes twelve 2D images 246, the bin 208 includes twelve 2D images 248, and the bin 210 includes twelve 2D images 250. As shown in FIG. 4, at least some of the non-motion corrected images 240 . . . 250 stored in the bins 200 . . . 210 include a feature 410 that appears as a black dot surrounded by a border. In the exemplary embodiment, each of the twelve images represent a different slice taken from the inferior side of the patient 16, shown as the upper right hand image in the set of twelve, to the superior side of the patient 16, shown as the last image in the set of twelve. However, it should be realized that any exemplary slices derived at any position may be displayed on the dashboard 400. Because, the sets of slices/images 240 . . . 250 are not motion corrected, the feature 410 may appear at different locations within the same bin.

In the exemplary embodiment, the dashboard 400 is also configured to display the motion corrected information stored in the bins 260 . . . 270. For example, as shown in FIG. 4, the bin 260 includes twelve 2D images 280, the bin 262 includes twelve 2D images 282, the bin 264 includes twelve 2D images 284, the bin 266 includes twelve 2D images 286, the bin 268 includes twelve 2D images 288, and the bin 270 includes twelve 2D images 290. As shown in FIG. 4, at least some of the motion corrected images 260 . . . 270 stored in the bins 280 . . . 210 also include the feature 410 that appears as a black dot surrounded by a border. In the exemplary embodiment, each of the twelve images, in each bin, represents a different slice taken from the inferior side of the patient 16, shown as the upper right hand image in the set of twelve, to the superior side of the patient 16, shown as the last image in the set of twelve. However, it should be realized that any exemplary slices derived at any position may be displayed on the dashboard 400. Because, the sets of slices/images 260 . . . 280 are now motion corrected, the feature 410 appears at approximately the same location within the same bin. Accordingly, the top portion of the dashboard 400 displays the non-motion corrected information, and the middle portion of the dashboard displays the motion corrected information that is formed by motion correcting each respective bin as described above. Moreover, because the feature 410 appears in approximately the same quantity of slices in each bin, e.g. eight slices in each bin, an operator may quickly determine that the motion correction procedure described above was successful by noting that the feature 410 appears in substantially the same location within each slice.

In the exemplary embodiment, the dashboard 100 may also display mixed sets of data. For example, the dashboard 400 may be configured to display the set 300 of non-motion corrected images that were formed by averaging the images from bins 200 . . . 210 as described above. In the exemplary embodiment, the dashboard 100 may also display mixed sets of data. The dashboard 400 may also be configured to display the set 302 of motion corrected images that were formed by averaging the motion corrected images from bins 240 . . . 250 as described above. Thus, the set of images 300 shows the feature 410 with no motion correction applied, and the set of images 302 shows the feature 410 after motion correction is applied.

In the exemplary embodiment, the dashboard 400 may also be configured to display other various items. For example, the dashboard 400 may be configured to display a surface rendering 420 of a non-motion corrected image that is generated sing the non-motion corrected images in the bins 200 . . . 210. The dashboard 400 may be configured to display a surface rendering 430 of a motion corrected image that is generated using the motion corrected images in the bins 260 . . . 270. The dashboard 400 may also be configured to display a surface rendering 440 of a non-motion corrected image that is generated using the non-motion corrected images in a single bin, such as for example, bin 200, 202, 204, 206, 208 or 210. The dashboard 400 may also be configured to display a surface rendering 450 of a motion corrected image that is generated using the motion corrected images in a single bin, such as for example, bin 260, 262, 264, 266, 268 or 270.

As shown in FIG. 4, the surface rendering 440 derived from a single bin, e.g. bin 210 traces a trajectory of the center of mass of the feature 410 on a cube to enable the operator to observe the range of motion of the feature 410. Moreover, the surface rendering 450 derived from a single bin, e.g. bin 270 traces a trajectory of the center of mass of the feature 410 on a cube to enable the operator to observe that the range of motion of the feature 410 is substantially zero indicating that the motion correction procedure described above was effective. Thus, the dashboard 400 is configured to display configurable combinations of both motion corrected images and non-motion corrected images to enable an operator to assess the effectiveness of the motion correction procedure.

Figure 5:
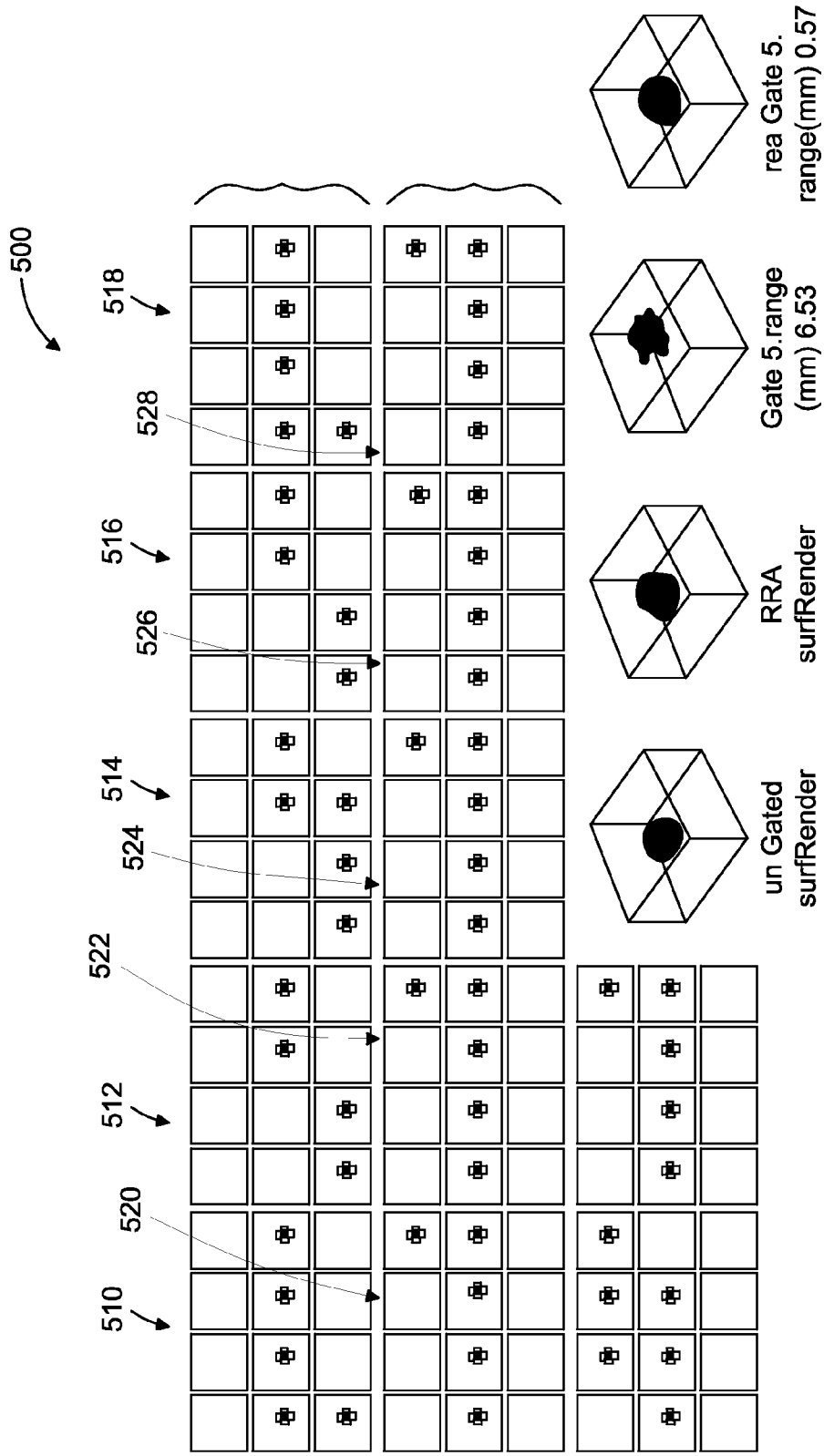
FIG. 5 is another dashboard that may be generated in accordance with various embodiments.

FIG. 5 is another exemplary dashboard 500 that may be generated at 118. The dashboard 500 is substantially similar to the dashboard 400 shown in FIG. 4. In the exemplary embodiment, the dashboard 500 is configured to display the information from five separate bins 510, 512, 514, 516, and 518. The dashboard 500 is configured to display, for example, non-motion corrected information from the bins 510 . . . 518 and motion corrected information from the bins 520 . . . 528. The dashboard 500 is also configured to display the various other images shown in FIG. 4. Thus, the dashboards 400 and 500 described herein may be configured to display any information that enables the operator to quickly and efficiently determine the effectiveness of the motion correction procedure. Moreover, the various images are all displayed concurrently such that the operator is not required to sort through large quantities of images to assess the motion correction procedure.

In the exemplary embodiment, the operator may determine which images are desired to enable the operator to assess the effectiveness of the motion correction procedure. For example, FIGS. 4 and 5 provide various exemplary images that may be displayed concurrently. The operator may then save the selected set of images as a macro, i.e. a short series of computer instructions, installed on the computer 44, for example. To initiate the macro, the operator may utilize a short-cut key or a short series of keys. For example, after the scanning is completed at 104, the operator may simply utilize a "one-touch" operation such as by depressing a short-cut key or clicking on an icon on the display 46, to display the gated data, the non-gated data, and the various other information on the display 46 in a format that has been previously selected by the operator.

Thus, each operator may create a customized display to enable the operator to evaluate a medical condition by displaying multiple slices that focus on the feature of interest 410. The operator may also quickly and efficiently evaluate the effectiveness of the motion correction procedure by observing the movement or non-movement of the feature 450 in several slices concurrently. In the exemplary embodiment, various other metrics may be displayed that enable an operator to quantify the size; shape, or location of the feature of interest 410.

A technical effect of some of the various embodiments described herein is to provide a fully or partially automatic method of displaying various images to enable an operator to determine the effectiveness of a motion correction procedure. The various embodiments enable an operator to view all the segmentations together for both gated and registered gated data to quickly visually assess that the segmentation, over all relevant slices, has occurred in a continuous manner. Additionally, an operator may click on any image on the dashboard to obtain a zoomed view of the information contained therein. All the information on the dashboard may be saved via a screen capture or a DICOM-compatible entity in order to be stored/networked for future use along with the regular patient data. Some of the various embodiments therefore provide a simple and quick method to analyze information that may be implemented into an existing clinical 4D PET-CT workflow and also improve the confidence of the operator by enabling the operator to efficiently review more data relevant to their diagnostic task. Thus, various embodiments described herein provide, for example, a method of generating a concise display of relevant lesion-centric quantitative and visual metrics from 4D image data, which includes 2D and 3D images over time.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for evaluating the effectiveness of a motion correction procedure, said method comprising:
   acquiring an imaging dataset of an object using an imaging system;
   identifying a motion affected portion of the imaging dataset;
   sorting the motion affected portion of the imaging dataset into a first plurality of motion affected images that are associated with a first bin and a second plurality of motion affected images that are associated with a second bin;
   motion correcting the motion affected portion to generate a motion corrected imaging dataset comprising first and second pluralities of motion corrected images associated with the first and second bins, respectively; and
   co-displaying first and second combinations, wherein the first combination comprises the first pluralities of motion affected and motion corrected images associated with the first bin, and the second combination comprises the second pluralities of motion corrected and motion affected images associated with the second bin.

2. The method of claim 1 wherein displaying further comprises concurrently displaying both the motion affected portion and the motion corrected imaging dataset on the display device.

3. The method of claim 1 further comprising concurrently displaying at least one of a surface rendering of a motion corrected image or a surface rendering of a non-motion corrected image with the motion corrected imaging dataset.

4. The method of claim 1 further comprising:
   generating an averaged image using the motion affected portion of the imaging dataset; and
   displaying the averaged image concurrently with the motion corrected imaging dataset.

5. The method of claim 1 further comprising:
   generating an averaged image using the motion corrected imaging dataset; and
   displaying the averaged image concurrently with the motion corrected imaging dataset.

6. The method of claim 1 further comprising
   sorting the motion affected portion of the imaging dataset that is affected by motion into a plurality of bins;
   selecting at least one of the plurality of bins as a reference bin; and
   motion correcting the motion affected portion based on the reference bin to generate the motion corrected imaging dataset.

7. The method of claim 1 wherein the first and second bins correspond to image data sorted based on a Quiescent Period Gating algorithm.

8. The method of claim 1 further comprising:
   arranging at least a portion of the motion affected portion and the motion corrected imaging dataset on the display device; and
   saving the arrangement as a dashboard to enable an operator to recreate the arrangement.

9. The method of claim 8 further comprising activating the dashboard using a short-cut key to recreate the arrangement.

10. The method of claim 1 wherein the co-displaying involves displaying the first and second combination of the motion affected and the corresponding motion corrected imaging dataset in at least one of a side-by-side or top-to-bottom arrangement.

11. A medical imaging system comprising a first modality unit and a computer operationally coupled to the first modality unit, wherein the computer is programmed to:

acquire an imaging dataset of an object using the medical imaging system;

identify a motion affected portion of the imaging dataset;

sort the motion affected portion of the imaging dataset into a first plurality of motion affected images that are associated with a first bin and a second plurality of motion affected images that are associated with a second bin;

motion correct the motion affected portion to generate a motion corrected imaging dataset comprising first and second pluralities of motion corrected images associated with the first and second bins, respectively; and co-display first and second combinations, wherein the first combination comprises the first pluralities of motion affected and motion corrected images associated with the first bin, and the second combination comprises the second pluralities of motion corrected and motion affected images associated with the second bin.

12. A medical imaging system in accordance with claim 11, wherein the computer is further programmed to concurrently display both the motion affected portion and the motion corrected imaging dataset on the display device.

13. A medical imaging system in accordance with claim 11, wherein the computer is further programmed to concurrently display at least one of a surface rendering of a motion corrected image or a surface rendering of a non-motion corrected image with the motion corrected imaging dataset.

14. A medical imaging system in accordance with claim 11, wherein the computer is further programmed to:

generate an averaged image using the motion affected portion of the imaging dataset that is affected by motion;

generate an averaged image using the motion corrected imaging dataset; and display the averaged images concurrently with the motion corrected imaging dataset.

15. A medical imaging system in accordance with claim 11, wherein the computer is further programmed to:

sort the motion affected portion of the imaging dataset into a plurality of bins;

select at least one of the plurality of bins as a reference bin; and motion correct the motion affected portion based on the reference bin to generate the motion corrected imaging dataset.

16. A medical imaging system in accordance with claim 11, wherein the computer is further programmed sort the image data corresponding to the first and second bins based a Quiescent Period Gating algorithm.

17. A medical imaging system in accordance with claim 11, wherein the computer is further programmed to:

receive an operator input that specifies an arrangement of at least a portion of the imaging dataset and the motion corrected imaging dataset on the display device;

save the arrangement as a dashboard to enable an operator to recreate the arrangement; and activate the dashboard based on an input from a short-cut key to recreate the arrangement.

18. The medical imaging system of claim 11, wherein the computer is further programmed to display the first and second combination of the motion affected and the corresponding motion corrected imaging dataset in at least one of a side-by-side or top-to-bottom arrangement.

19. A non-transitory computer readable medium encoded with a program programmed to instruct a computer to:

acquire an imaging dataset of an object using the medical imaging system;

identify a motion affected portion of the imaging dataset;

sort the motion affected portion of the imaging dataset into a first plurality of motion affected images that are associated with a first bin and a second plurality of motion affected images that are associated with a second bin;

motion correct the motion affected portion to generate a motion corrected imaging dataset comprising first and second pluralities of motion corrected images associated with the first and second bins, respectively; and co-display first and second combinations, wherein the first combination comprises the first pluralities of motion affected and motion corrected images associated with the first bin, and the second combination comprises the second pluralities of motion corrected and motion affected images associated with the second bin.

20. A nontransitory computer readable medium in accordance with claim 19, said computer readable medium is further programmed to instruct a computer to concurrently display both the motion affected portion, the motion corrected imaging dataset, and at least one of a surface rendering of a motion corrected image or a surface rendering of a non-motion corrected image on the display.

21. A nontransitory computer readable medium in accordance with claim 19, said computer readable medium is further programmed to instruct a computer to:

generate an averaged image using the motion affected portion of the imaging dataset that is affected by motion;

generate an averaged image using the motion corrected imaging dataset; and display the averaged images concurrently with the motion corrected imaging dataset.

22. A nontransitory computer readable medium in accordance with claim 19, said computer readable medium is further programmed to instruct a computer to:

receive an operator input that specifies an arrangement of at least a portion of the imaging dataset and the motion corrected imaging dataset on the display device;

save the arrangement as a dashboard to enable an operator to recreate the arrangement; and activate the dashboard based on an input from a short-cut key.

23. The nontransitory computer readable medium in accordance with claim 19, the computer readable medium is further programmed to instruct the computer to display the first and second combination of the motion affected and the corresponding motion corrected imaging dataset in at least one of a side-by-side or top-to-bottom arrangement.

\* \* \* \* \*